United States Patent
Tuffin et al.

(10) Patent No.: US 6,337,327 B1
(45) Date of Patent: Jan. 8, 2002

(54) PHARMACEUTICAL COMPOSITIONS COMPRISING AN ALDOSE REDUCTASE INHIBITOR AND AN ACE INHIBITOR

(75) Inventors: David Patrick Tuffin; Frank Carey, both of Macclesfield; Mary Anne Cotter; Norman Eugene Cameron, both of Aberdeen, all of (GB)

(73) Assignee: Zeneca Limited, London (GB)

(*) Notice: Subject to any disclaimer, the term of this patent is extended or adjusted under 35 U.S.C. 154(b) by 0 days.

(21) Appl. No.: 09/462,353

(22) PCT Filed: Jul. 2, 1998

(86) PCT No.: PCT/GB98/01959

§ 371 Date: Jan. 7, 2000

§ 102(e) Date: Jan. 7, 2000

(87) PCT Pub. No.: WO99/02189

PCT Pub. Date: Jan. 21, 1999

(30) Foreign Application Priority Data

Jul. 8, 1997 (GB) .............................. 9714274

(51) Int. Cl.⁷ .................. A61K 31/54; A61K 31/50; A61K 31/505; A61K 31/425; A61K 31/40

(52) U.S. Cl. .................. 514/226.5; 514/247; 514/259; 514/367; 514/409; 514/431; 514/451; 514/474; 514/518

(58) Field of Search .............................. 514/474, 226.5, 514/247, 259, 367, 409, 431, 451, 518

(56) References Cited

U.S. PATENT DOCUMENTS 6,069,168 A * 5/2000 Horrobin et al. ............ 514/474

FOREIGN PATENT DOCUMENTS

EP 0 469 887 2/1996

OTHER PUBLICATIONS

Goldfarb et al: "Effect of polyol pathway inhibition and dietary myo inositol on glomerular hemodynamic function in experimental diabetes mellitus in rats" Diabetes, vol. 40, No. 4, 1991, pp. 465–471, XP02080592 see p. 467, col. 2, paragraph 3, p. 468, col. 1, paragraph 1.

Scott, R.S: "Prevention of diabetic complications" New Ethicals, vol. V32, Nov. 1995, p. 15–20 XP002080593 see p. 20, col. 1, paragraph 3–4.

Cameron et al.; "Angiotensin converting enzyme inhibition prevents development of muscle and nerve dysfunction and stimulates angiogenesis in streptozotocin–diabetic rats"; Diabetologia, vol. 35, 1992, pp. 12–18.

Cameron et al., "Aldose reductase inhibition, nerve perfusion, oxygenation and function in streptozotocin–diabetic rats: dose–response considerations and independence from a myo–inositol mechanism"; Diabetologia; vol. 37, pp. 651–663.

Cameron et al.; :The Effect of Aldose Reductase Inhibition on the Pattern of Nerve Conduction Deficits in Diabetic Rats; Quarterly Journal of Experimental Physiology, 1989, pp. 917–926.

Goldfarb et al.; "Effects of Polyol–Pathway Inhibition and Dietary myo–Inositol on Glomerular Hemodynamic Function in Expermental Diabetes Mellitus in Rats", Diabetes, vol. 40, 1991, pp. 465–471.

Scott; "Prevention of Diabetic Complications"; New Ethicals, vol. 32, Nov. 1995; pp. 15–20.

* cited by examiner

*Primary Examiner*—Kevin E. Weddington
(74) *Attorney, Agent, or Firm*—Pillsbury Winthrop LLP

(57) ABSTRACT

The invention relates to pharmaceutical compositions comprising an aldose reductase inhibitor and an ACE inhibitor, and their use in the treatment of diabetic complications such as diabetic neuropathy, diabetic retinopathy and diabetic nephropathy.

11 Claims, No Drawings

PHARMACEUTICAL COMPOSITIONS COMPRISING AN ALDOSE REDUCTASE INHIBITOR AND AN ACE INHIBITOR

The present invention relates to pharmaceutical compositions, and in particular to pharmaceutical compositions containing an aldose reductase inhibitor (ARI) and an angiotensin converting enzyme (ACE) inhibitor, which are useful in the prevention and treatment of the complications of diabetes mellitus.

Diabetes mellitus is a chronic disease characterised by hyperglycemia and by complications that include diabetic nephropathy, diabetic neuropathy, diabetic retinopathy, diabetic cataract and the like. While various investigators have studied the use of ACE inhibitors or aldose reductase inhibitors independently in such conditions, none have proposed the combination therapy provided by the present invention.

Prolonged administration of an ACE inhibitor at a therapeutically effective dose may be deleterious or give rise to side effects in certain patients, for example it may lead to significant deterioration of renal function, induce hyperkalemia, neutropenia, angioneurotic oedema, rash or diarrhoea or give rise to a dry cough. Administration of an ARI may also give rise to deleterious effects or side effects at the dose required to inhibit the enzyme aldose reductase sufficiently to produce a significant beneficial therapeutic effect. The present invention lessens the problems associated with administration of an ARI or an ACE inhibitor alone and/or provides a means for obtaining a therapeutic effect which is significantly greater than that otherwise obtainable with the single agents when administered alone. Furthermore, diabetic complications involve a complex mechanism or number of mechanisms, which initiate a cascade of biochemical alterations that in turn lead to structural changes. These may result in a diverse patient population. The present invention therefore provides the additional advantage that it allows tailoring of treatment to the needs of a particular patient population.

Accordingly the present invention provides a pharmaceutical composition which comprises an aldose reductase inhibitor and an ACE inhibitor, together with a pharmaceutically acceptable carrier and/or diluent.

Suitable aldose reductase inhibitors useful in the compositions of the present invention include, for example, epalrestat, tolrestat, ponolrestat, zopolrestat, AD-5467, SNK-860, ADN-138, AS-3201, zenarestat, sorbinil, methosorbinil, imirestat, minalrestat (WAY-121509) and ZD5522 (3',5'-dimethyl-4'-nitromethylsulfonyl-2-(2-tolyl) acetanilide, prepared as described in European Patent Application, Publication No. 469887, Examples 3 and 60), or a pharmaceutically acceptable salt thereof. A preferred aldose reductase inhibitor includes, for example, ZD5522.

Suitable ACE inhibitors useful in the compositions of the present invention include, for example, benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril, and cilazapril, or a pharmaceutically acceptable salt thereof. A preferred ACE inhibitor includes, for example, lisinopril.

Independent aspects of the present invention include a pharmaceutical composition which comprises any one of the named aldose reductase inhibitors identified above and any one of the named ACE inhibitors identified above, together with a pharmaceutically acceptable carrier and/or diluent.

Accordingly, further independent aspects of the present invention include the following:

(1) A pharmaceutical composition which comprises epalrestat and lisinopril, together with a pharmaceutically acceptable carrier and/or diluent;

(2) A pharmaceutical composition which comprises tolrestat and lisinopril, together with a pharmaceutically acceptable carrier and/or diluent;

(3) A pharmaceutical composition which comprises ponolrestat and lisinopril, together with a pharmaceutically acceptable carrier and/or diluent;

(4) A pharmaceutical composition which comprises zopolrestat and lisinopril, together with a pharmaceutically acceptable carrier and/or diluent;

(5) A pharmaceutical composition which comprises AD-5467 and lisinopril, together with a pharmaceutically acceptable carrier and/or diluent;

(6) A pharmaceutical composition which comprises SNK-860 and lisinopril, together with a pharmaceutically acceptable carrier and/or diluent;

(7) A pharmaceutical composition which comprises ADN-138 and lisinopril, together with a pharmaceutically acceptable carrier and/or diluent;

(8) A pharmaceutical composition which comprises AS-3201 and lisinopril, together with a pharmaceutically acceptable carrier and/or diluent;

(9) A pharmaceutical composition which comprises zenarestat and lisinopril, together with a pharmaceutically acceptable carrier and/or diluent;

(10) A pharmaceutical composition which comprises sorbinil and lisinopril, together with a pharmaceutically acceptable carrier and/or diluent;

(11) A pharmaceutical composition which comprises methosorbinil and lisinopril, together with a pharmaceutically acceptable carrier and/or diluent;

(12) A pharmaceutical composition which comprises imirestat and lisinopril, together with a pharmaceutically acceptable carrier and/or diluent; and

(13) A pharmaceutical composition which comprises minalrestat and lisinopril, together with a pharmaceutically acceptable carrier and/or diluent.

A preferred pharmaceutical composition of the invention comprises the aldose reductase inhibitor ZD5522, or a pharmaceutically acceptable salt thereof, and an ACE inhibitor (including any of the ACE inhibitors specifically named above), together with a pharmaceutically acceptable carrier and/or diluent.

An especially preferred pharmaceutical composition of the invention comprises the aldose reductase inhibitor ZD5522, or a pharmaceutically acceptable salt thereof, and the ACE inhibitor lisinopril, or a pharmaceutically acceptable salt thereof, together with a pharmaceutically acceptable diluent and/or carrier.

Pharmaceutically acceptable salts of the aldose reductase inhibitors and of the ACE inhibitors, in accordance with the present invention, are the salts with physiologically acceptable bases and/or acids well known to those skilled in the art of pharmaceutical technique. Suitable salts with physiologically acceptable bases include, for example, alkali metal and alkaline earth metal salts, such as sodium, potassium, calcium and magnesium salts, and ammonium salts and salts with suitable organic bases, such as methylamine, dimethylamine, trimethylamine, piperidine, morpholine and triethanolamine. Suitable salts with physiologically acceptable acids include, for example, salts with inorganic acids such as hydrohalides (especially hydrochlorides or hydrobromides), sulphates and phosphates, and salts with organic acids.

The pharmaceutical compositions of the present invention may be administered in standard manner for example by oral or parenteral administration, using conventional systemic dosage forms, such as a tablets, capsules, pills, powders, aqueous or oily solutions or suspensions, emulsions, sterile injectable aqueous or oily solutions or suspensions. These dosage forms will include the necessary carrier material, excipient, lubricant, buffer, bulking agent, anti-oxidant, dispersant or the like.

In particular, compositions for oral administration are preferred.

The doses of an aldose reductase inhibitor and an ACE inhibitor which can be administered in accordance with the present invention depends on several factors, for example the age, weight and the severity of the condition under treatment, as well as the route of administration, dosage form and regimen and the desired result, and additionally the potency of the particular aldose reductase inhibitor and ACE inhibitor employed in the composition. In addition, account should be taken of the recommended maximum daily dosages for the ACE inhibitors.

A unit dosage formulation such as a tablet or capsule will usually contain, for example, from 0.1 mg to 500 mg of an aldose reductase inhibitor and from 0.1 mg to 500 mg of an ACE inhibitor. Preferably a unit dose formulation will contain 0.1 to 100 mg of an aldose reductase inhibitor and 0.1 to 100 mg of an ACE inhibitor.

The pharmaceutical compositions of the present invention may be administered up to six times daily, conveniently 1 to 4 times daily and preferably 1 to 2 times daily, so that a dose of the aldose reductase inhibitor in the general range of 0.01 to 100 mg/kg, preferably 0.1 to 10 mg/kg, more preferably 0.1 to 5 mg/kg, is administered daily and a dose of ACE inhibitor in the general range 0.01 to 100 mg/kg, preferably 0.01 to 20 mg/kg, more preferably 0.01 to 1 mg/kg, is administered daily.

The present invention covers the combination of (or product containing) an aldose reductase inhibitor and an ACE inhibitor for simultaneous, separate or sequential use in the treatment of diabetic complications. In one aspect of the present invention, the aldose reductase inhibitor or a pharmaceutically acceptable salt thereof and an ACE inhibitor or a pharmaceutically acceptable salt thereof are presented in admixture in one pharmaceutical dosage form. In another aspect, the present invention covers the administration of separate unit dosages of the aldose reductase inhibitor and the ACE inhibitor in order to achieve the desired therapeutic effect. Such separate unit dosages may be administered concurrently or sequentially as determined by the clinician. Preferably the aldose reductase inhibitor and the ACE inhibitor are both administered orally. The present invention also covers an agent for the treatment of diabetic complications comprising a pharmaceutically acceptable carrier and/or diluent and, as active agents, an aldose reductase inhibitor and an ACE inhibitor in quantities producing a synergistic therapeutic effect.

In another aspect of the invention there is provided a combination of pharmaceutical compositions for combination therapy of diabetic complications, the combination consisting of a pharmaceutical composition comprising an aldose reductase inhibitor and a pharmaceutical composition comprising an ACE inhibitor. Particular diabetic complications include, for example, diabetic neuropathy, diabetic nephropathy and diabetic retinopathy.

A further aspect of the present invention comprises the use of an aldose reductase inhibitor and an ACE inhibitor in the preparation of a pharmaceutical composition for use in the treatment of diabetic complications.

A further aspect of the present invention is a method for treating diabetic complications (such is diabetic neuropathy, diabetic nephropathy or diabetic retinopathy) wherein a therapeutically effective amount of an aldose reductase inhibitor in combination with an ACE inhibitor is administered systemically, such as orally or parenterally. Where the patient to be treated is normotensive, the ACE inhibitor will preferably be administered in amounts below that required to cause a reduction in blood pressure. Where the patient to be treated is hypertensive, the ACE inhibitor will preferably be used in amounts usually employed to treat hypertension. The present invention provides a novel method for treating diabetic complications and the amounts of aldose reductase and ACE inhibitor required when administered in association with the combined therapy are lower than would normally be used, and thus any deleterious effects or side effects are minimised.

The effect of a pharmaceutical composition of the present invention may be examined by using one or more of the published models of diabetic complications well known in the art. The pharmaceutical compositions of the present invention are particularly useful for the prevention of, reducing the development of, or reversal of, deficits in nerve function found in diabetic patients, and therefore particularly useful in the treatment of diabetic neuropathy. This may be demonstrated, for example, by measuring markers such as nerve conduction velocity, nerve amplitude, quantitative sensory testing, autonomic function testing and morphometric changes. Experimentally, studies analogous to those described in Diabetologia, 1992, Vol. 35, pages 12–18 and 1994, Vol. 37, pages 651–663 may be carried out.

A further aspect of the present invention is a method of treating or preventing the development of disease conditions associated with impaired neuronal conduction velocity in a warm-blooded animal (including a human being) requiring such treatment which comprises administering to said animal a therapeutically effective amount of a combination of an aldose reductase inhibitor and an ACE inhibitor. A further aspect of the present invention is the use of an aldose reductase inhibitor and an ACE inhibitor for the manufacture of a medicament for use in the treatment or prevention of the development of disease conditions associated with impaired neuronal conduction velocity.

A further aspect of the present invention is a method of reversing impaired neuronal conduction velocity in a warm-blooded animal (including a human being) requiring such treatment which comprises administering to said animal a therapeutically effective amount of a combination of an aldose reductase inhibitor and an ACE inhibitor. A further aspect of the present invention is the use of an aldose reductase inhibitor and an ACE inhibitor for the manufacture of a medicament for use in the reversal of impaired neuronal conduction velocity.

The following non-limiting Examples serve to illustrate the present invention.

EXAMPLE 1

Suitable pharmaceutical compositions of an aldose reductase inhibitor (ARI), such as ZD5522, include the following:

| | mg/tablet |
|---|---|
| Tablet 1 | |
| ARI | 100 |
| Lactose Ph. Eur. | 182.75 |
| Croscarmellose sodium | 12.0 |
| Maize starch paste (5% w/v paste) | 2.25 |
| Magnesium stearate | 3.0 |
| Tablet 2 | |
| ARI | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| Tablet 3 | |
| ARI | 1.0 |
| Lactose Ph. Eur. | 93.25 |
| Croscarmellose sodium | 4.0 |
| Maize starch paste (5% w/v paste) | 0.75 |
| Magnesium stearate | 1.0 |
| Capsule 1 | |
| ARI | 10 |
| Lactose Ph. Eur. | 488.5 |
| Magnesium stearate | 1.5 |

EXAMPLE 2

Suitable pharmaceutical compositions of an ACE inhibitor include the following:

| | Tablet |
|---|---|
| Tablet 1 | |
| ACE Inhibitor | 100 |
| Corn starch | 50 |
| Gelatin | 7.5 |
| Microcrystalline cellulose | 25 |
| Magnesium stearate | 2.5 |
| Tablet 2 | |
| ACE inhibitor | 20 |
| Pregelatinised starch | 82 |
| Microcrystalline cellulose | 82 |
| Magnesium stearate | 1 |

EXAMPLE 3

Suitable pharmaceutical compositions containing an ARI and an ACE inhibitor in a single dosage form include the following:

| | Tablet |
|---|---|
| ARI | 70 |
| ACE inhibitor | 10 |
| Corn starch | 40 |
| Gelatin | 6 |
| Microcrystalline cellulose | 20 |
| Magnesium stearate | 2.0 |

EXAMPLE 4

A patient requiring treatment for diabetic neuropathy is treated with ZD5522 (70 mg) and lisinopril (10 mg). Each compound is administered twice daily.

EXAMPLE 5

Male Sprague-Dawley rats, 19 weeks old at the start of the study, were divided into non-diabetic animals (normal control group) and animals rendered diabetic by intraperitoneal administration of streptozotocin, (40–45 mg/kg, freshly dissolved in sterile saline). Diabetes was verified 24 hours later by estimating hyperglycemia and glucosuria (Visidex II and Diastix; Ames, Slough, UK). Diabetic rats were tested weekly and weighed daily. Animals were rejected if the plasma glucose concentration was <20 mM of if body weight consistently increased over 3 days. Samples were taken from the tail vein or carotid artery after final experiments for plasma glucose determination (GOD-Perid method; Boehringer Mannheim, Mannheim, Germany). After 6 weeks of untreated diabetes, groups of rats were treated for a further 2 weeks with lisinopril (0.3 mg/kg/day) or the aldose reductase inhibitor, ZD5522 (0.25 mg/kg/day) or a combination of the two drugs, dissolved in the drinking water.

At the end of the treatment period, rats were anesthetized with thiobutabarbitone by intraperitoneal injection (50–100 mg/kg). The trachea was cannulated for artificial ventilation and a cartoid cannula was used to monitor mean systemic blood pressure. Motor nerve conduction velocity was measured (as previously described by Cameron et al, Diabetologia, 1993, Vol. 36, pages 299–304) between sciatic notch and knee in the nerve branch to tibialis anterior muscle, which is representative of the whole sciatic nerve in terms of susceptibility to diabetes and treatment effects.

RESULTS

Nerve conduction velocity (mean±SEM) was 64.4±0.5 m/s in nondiabetic control rats and this was reduced to 50.9±0.5 m/s with untreated diabetes ($p<0.001$). Treatment with lisinopril or ZD5522 produced small (~20%) but statistically significant increases in conduction velocity to 53.9±0.6 ($p<0.01$) and 53.7±0.3 ($p<0.001$) m/s respectively. With joint treatment, conduction velocity was within the nondiabetic range, 63.85±0.41 ($p<0.001$ vs the diabetic control group). This conduction velocity increment was considerably greater than that predicted from simple addition of the effects of the two drugs (56.1 m/s, $p<0.0001$, one sample t-test).

What we claim is:

1. The pharmaceutical composition which comprises an aldose reductase inhibitor and an angiotensin converting enzyme inhibitor, together with a pharmaceutically acceptable carrier and/or diluent.

2. The pharmaceutical composition as claimed in claim 1 wherein the aldose reductase inhibitor is selected from epalrestat, tolrestat, ponolrestat, zopolrestat, AD-5467, SNK-860, ADN-138, AS-3201, zenarestat, sorbinil, methosorbinil, imirestat, minalrestat and ZD5522, or a pharmaceutically acceptable salt thereof.

3. The pharmaceutical composition as claimed in claim 1 wherein the angiotensin converting enzyme inhibitor is selected from benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril and cilazapril, or a pharmaceutically acceptable salt thereof.

4. The pharmaceutical composition as claimed in claim 1, wherein the aldose reductase inhibitor is ZD5522, or a pharmaceutically acceptable salt thereof.

5. The pharmaceutical composition as claimed in claim 1, wherein the angiotensin converting enzyme inhibitor is lisinopril, or a pharmaceutically acceptable salt thereof.

6. The pharmaceutical composition as claimed in claim 2 wherein the angiotenisin converting enzyme inhibitor is selected from benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril and cilazapril, or a pharmaceutically acceptable salt thereof.

7. The pharmaceutical composition as claimed in claim 3 wherein the aldose reductase inhibitor is ZD5522, or a pharmaceutically acceptable salt thereof.

8. The pharmaceutical composition as claimed in claim 2 wherein the angiotensin converting enzyme inhibitor is lisinopril, or a pharmaceutically acceptable salt thereof.

9. The pharmaceutical composition as claimed in claim 4 wherein the angiotensin converting enzyme inhibitor is lisinopril, or a pharmaceutically acceptable salt thereof.

10. A method of treating diabetic complications in a warm blooded animal in need thereof comprising administering a treatment-sufficient amount of the pharmaceutical composition as claimed in any one of claims 1, 7 or 9.

11. A method of treating diabetic neuropathy in a warm blooded animal in need thereof comprising administering a treatment-sufficient amount of the pharmaceutical composition as claimed in any one of claims 1, 7 or 9.

\* \* \* \* \*